(12) United States Patent
Watkins et al.

(10) Patent No.: US 7,813,638 B2
(45) Date of Patent: Oct. 12, 2010

(54) SYSTEM FOR GENERATING CAMERA TRIGGERS

(75) Inventors: Cory Watkins, Chanhassen, MN (US); David Bocek, Plymouth, MN (US)

(73) Assignee: Rudolph Technologies, Inc., Flanders, NJ (US)

( * ) Notice: Subject to any disclaimer, the term of this patent is extended or adjusted under 35 U.S.C. 154(b) by 665 days.

(21) Appl. No.: 11/146,301

(22) Filed: Jun. 6, 2005

(65) Prior Publication Data

US 2005/0276595 A1 Dec. 15, 2005

Related U.S. Application Data

(60) Provisional application No. 60/577,544, filed on Jun. 7, 2004.

(51) Int. Cl.
*G03B 17/00* (2006.01)
(52) U.S. Cl. ...................... 396/263; 348/126
(58) Field of Classification Search ................. 396/263; 382/145; 348/123
See application file for complete search history.

(56) References Cited

U.S. PATENT DOCUMENTS

| | | | | |
|---|---|---|---|---|
| 5,018,212 A * | 5/1991 | Manns et al. | ............... | 382/145 |
| 6,167,148 A * | 12/2000 | Calitz et al. | ................. | 382/145 |
| 6,362,877 B1 * | 3/2002 | Kobayashi et al. | ....... | 356/237.5 |
| 6,363,168 B1 * | 3/2002 | Kakuma | ..................... | 382/151 |
| 6,847,730 B1 * | 1/2005 | Beer et al. | .................. | 382/145 |
| 7,215,808 B2 * | 5/2007 | Miller | ........................ | 382/145 |
| 2001/0053242 A1 * | 12/2001 | Okada | ........................ | 382/145 |
| 2002/0021837 A1 * | 2/2002 | Suzuki | ....................... | 382/181 |
| 2002/0100872 A1 * | 8/2002 | Hiroi et al. | .................. | 250/310 |
| 2002/0186877 A1 * | 12/2002 | Vilella | ........................ | 382/145 |
| 2003/0063790 A1 * | 4/2003 | Smilansky et al. | .......... | 382/145 |
| 2003/0193571 A1 * | 10/2003 | Schultz et al. | ......... | 348/207.99 |

\* cited by examiner

*Primary Examiner*—W. B. Perkey
*Assistant Examiner*—Fang-Chi Chang
(74) *Attorney, Agent, or Firm*—Dicke, Billig & Czaja, PLLC

(57) ABSTRACT

A system for generating a camera trigger that causes a camera to capture image data includes a memory for storing a plurality of trigger values. Each trigger value corresponds to a position of a moving stage. The system includes a controller for receiving position information indicative of a current position of the moving stage, generating a current position value based on the position information, comparing the current position value to at least one of the trigger values, and generating a camera trigger if the current position value matches one of the trigger values.

21 Claims, 4 Drawing Sheets

SYSTEM FOR GENERATING CAMERA TRIGGERS

CROSS-REFERENCE TO RELATED APPLICATIONS

This application claims the benefit under § 119(e)(1), and incorporates herein by reference an entirety of, U.S. Provisional Application No. 60/577,544, filed Jun. 7, 2004 and entitled "System for Generating Camera Triggers".

BACKGROUND

1. Technical Field

The present invention relates to machine vision and specifically the frame grabber or camera triggers used therein.

2. Background Information

Over the past several decades, the semiconductor has exponentially grown in use and popularity. The semiconductor has in effect revolutionized society by introducing computers, electronic advances, and generally revolutionizing many previously difficult, expensive and/or time consuming mechanical processes into simplistic and quick electronic processes. This boom in semiconductors has been fueled by an insatiable desire by business and individuals for computers and electronics, and more particularly, faster, more advanced computers and electronics whether it be on an assembly line, on test equipment in a lab, on the personal computer at one's desk, or in the home electronics and toys.

The manufacturers of semiconductors have made vast improvements in end product quality, speed and performance as well as in manufacturing process quality, speed and performance. However, there continues to be demand for faster, more reliable and higher performing semiconductors. To assist these demands, better inspection is necessary to increase yields.

To increase such yields, accurate and fast defect inspection is needed. One component of a typical defect inspection system is a machine vision frame grabber or camera triggering mechanism which is commonly provided as a feature of the motion controller. In such systems, a digital signal processor (DSP) with associated software is typically used to generate camera triggers. In these systems, trigger position updating (and in many cases the triggers themselves) are typically limited by the motion controller servo cycle and processing overhead. It is not uncommon for triggers to be delayed or missed entirely in demanding applications. This interferes with the accurate and fast inspection demands of the users of defect inspection systems.

SUMMARY

One form of the present invention provides a system for generating a camera trigger that causes a camera to capture image data. The system includes a memory for storing a plurality of trigger values. Each trigger value corresponds to a position of a moving stage. The system includes a controller for receiving position information indicative of a current position of the moving stage, generating a current position value based on the position information, comparing the current position value to at least one of the trigger values, and generating a camera trigger if the current position value matches one of the trigger values.

BRIEF DESCRIPTION OF THE DRAWINGS

Preferred embodiment of the invention, illustrative of the best mode in which applicant has contemplated applying the principles, are set forth in the following description and are shown in the drawings and are particularly and distinctly pointed out and set forth in the appended claims.

Similar numerals refer to similar parts throughout the drawings.

DETAILED DESCRIPTION

Figure 1:
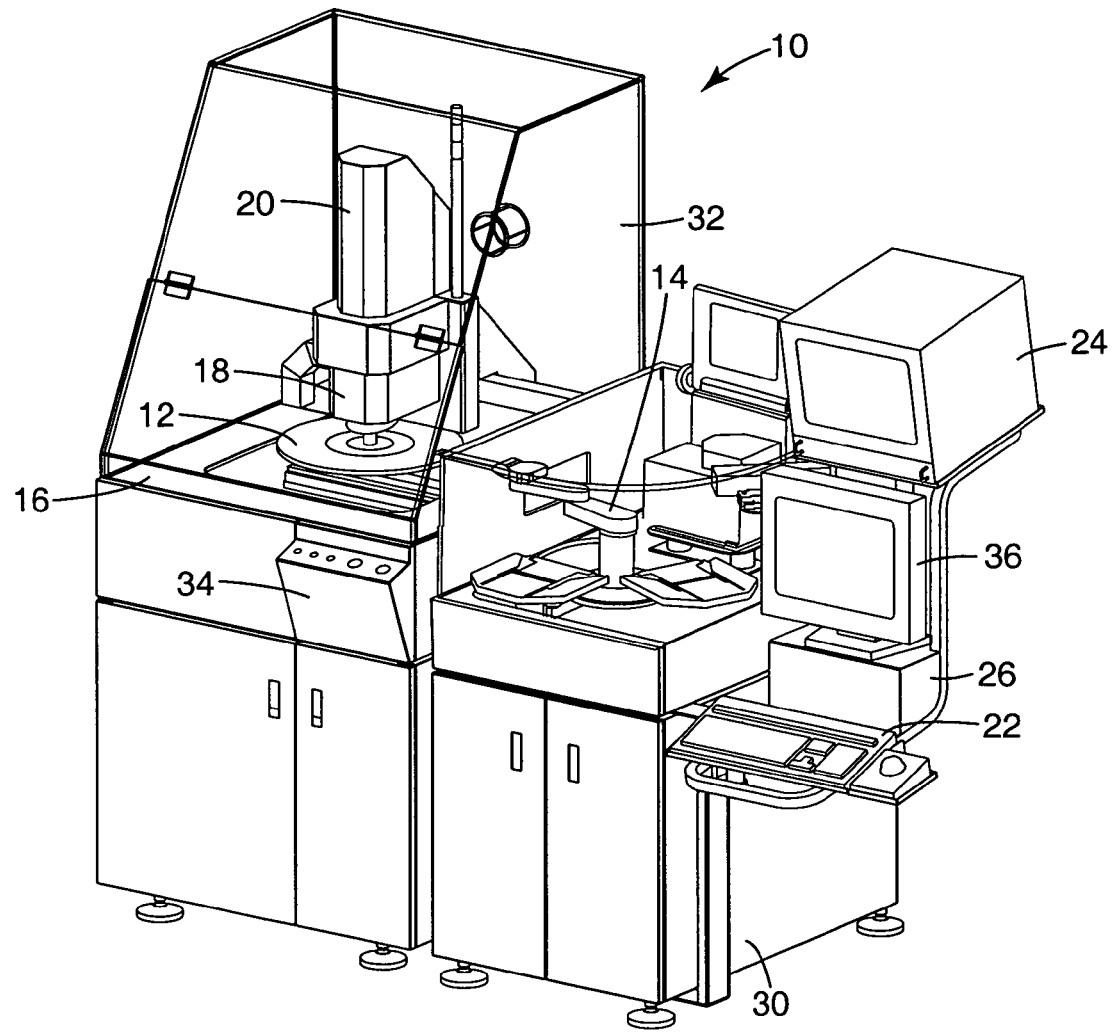
FIG. 1 is a diagram illustrating an automated defect inspection system according to one embodiment of the present invention.

FIG. 1 is a diagram illustrating an automated defect inspection system 10 according to one embodiment of the present invention. System 10 is used in one environment to find defects on die on patterned wafers W, but is intended for this and other uses including for inspecting whole wafers, sawn wafers, broken wafers, wafers of any kind on film frames, die in gel paks, die in waffle paks, MCMs, JEDEC trays, Auer boats, and other wafer and die package configurations (although hereinafter all of these uses shall be referred to generally as inspection of wafers W). The basic operation of system 10 according to one embodiment is described in detail in commonly-assigned U.S. Pat. No. 6,324,298, and is summarized below with reference to FIG. 1.

System 10 includes a wafer test plate 12, means for providing a wafer to the test plate referred to as 14, a wafer alignment device 16 for aligning each and every wafer at the same x, y, and θ location or x, y, z, and θ location, a focusing mechanism 18, a camera 20 or other visual inspection device for visual inputting of good die during training and for visual inspection of other unknown quality die during inspection, a parameter input device 22 for inputting parameters and other constraints or information such as sensitivity parameters, geometries, die size, die shape, die pitch, number of rows, number of columns, etc., a display 24 for displaying the view being seen by the camera presently or at any previously saved period, a computer system 26 or other computer-like device having processing and memory capabilities for saving the inputted good die, developing a model therefrom, and comparing or analyzing other die in comparison to the model, a frame 30, a hood 32, a control panel 34, and a system parameters display 36.

The means for providing a wafer to the test plate referred to as 14 may be either manual in that the user moves the wafer from a cassette or magazine to the test plate 12, or automatic as is shown in the embodiment of FIG. 1. In the automatic environment, the wafer providing means 14 includes a robotic arm that pivots from a first position where a wafer W is initially grasped from a magazine or cassette to a second position where the wafer W is positioned on the wafer test plate 12 for inspection. After inspection, the robotic arm pivots the wafer W from the second position at the test plate 12 back to the first position where the wafer W is placed back in or on the magazine or cassette.

In one form of the invention, system 10 is trained as to what a "good die" comprises by aligning via device 16 and viewing via camera 20 a plurality of known good die and forming a model within computer system 26 to define what an ideal die should look like based upon the common characteristics viewed. In one embodiment, after being trained, system 10 is used to inspect die of unknown quality. During inspection according to one embodiment, system 10 collects an image of a wafer W using the camera 20 by moving the plate 12 to align the camera with a first die or other portion thereof, viewing and recording that die or portion thereof by opening the shutter and allowing the camera to view and record the image, moving the plate 12 to align the camera with a second die or portion thereof, viewing and recording the second die or portion thereof, and repeating these steps until all of the die or portions thereof on the wafer that are desired to be viewed have been viewed and recorded. In one embodiment, system 10 determines where defects are located on a given die being viewed based upon the "good die" model.

In another embodiment, rather than using a stop and go procedure to capture images of die on the wafer W, system 10 collects an image of the wafer W using the camera 20 by continuously moving the plate 12 so as to scan over all of the die on the wafer, whereby the wafer is illuminated by a strobe light at a sequence correlating to the speed of the moving plate so that each die is strobed at the precise time it is under the camera 20. This allows for the continuous collecting of images without necessitating the stop and go procedure of aligning the camera with a first die, viewing and recording that die, moving the plate 12 to align the camera with a second die, viewing and recording this second die, and repeating these steps until all of the die on the wafer have been viewed and recorded, etc.

Figure 2:
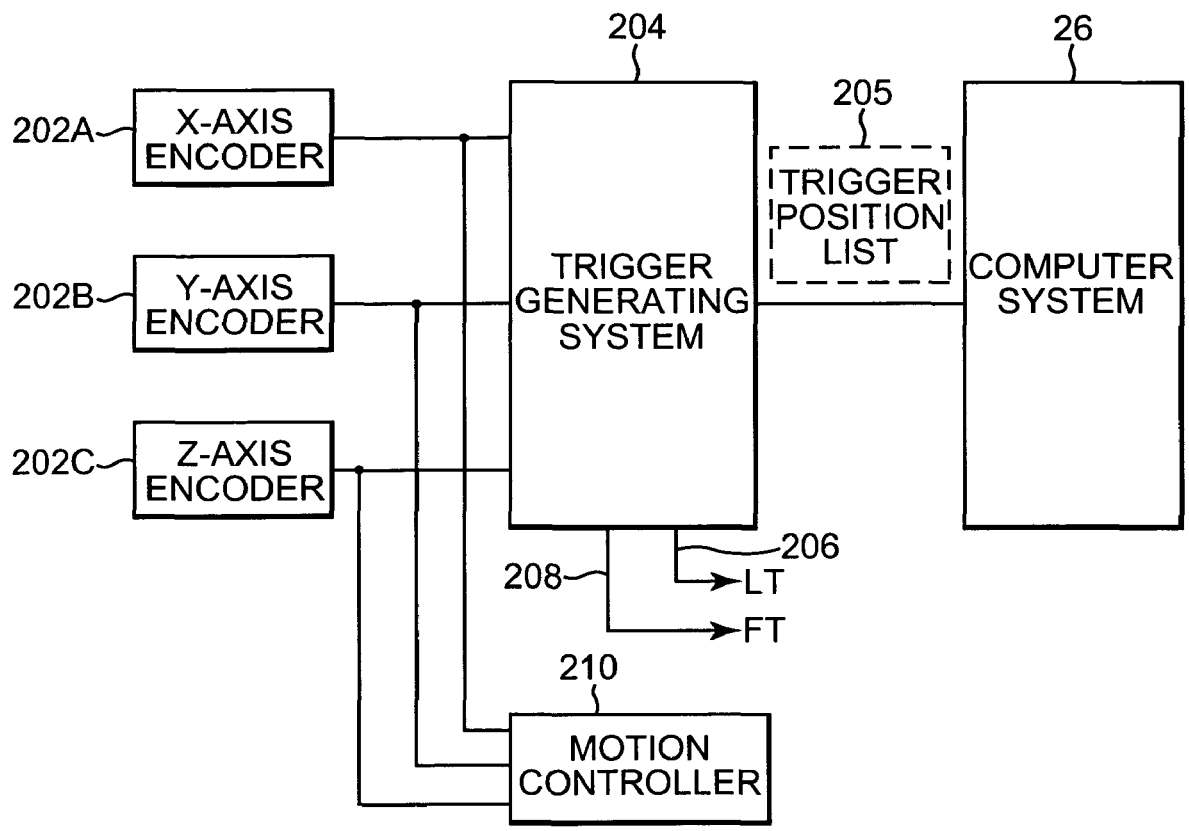
FIG. 2 is a block diagram illustrating major components of the automated defect inspection system shown in FIG. 1 according to one embodiment of the present invention.

FIG. 2 is a block diagram illustrating major components of the automated defect inspection system 10 shown in FIG. 1 according to one embodiment of the present invention. System 10 includes X-axis encoder 202A, Y-axis encoder 202B, Z-axis encoder 202C, trigger generating system 204, computer system 26, and motion controller 210. In one embodiment, X-axis encoder 202A, Y-axis encoder 202B, and Z-axis encoder 202C (collectively referred to as encoders 202) are quadrature encoders that monitor the position of plate 12 (FIG. 1), and that each generate phase A and phase B encoder signals. The encoder signals output by encoders 202 are used to determine the current position of plate 12 in three dimensions X, Y, and Z. The encoder signals generated by encoders 202 are output to trigger generating system 204 and to motion controller 210. Motion controller 210 receives the encoder signals from each of the three encoders 202, and based on the received signals, controls the position of plate 12.

Trigger generating system 204 also receives the encoder signals from each of the three encoders 202, and based on the received signals, generates trigger signals that indicate to camera 20 (FIG. 1) when to capture an image. In one form of the invention, camera 20 includes a linear sensor array for capturing lines of image data, and trigger generating system 204 generates line trigger (LT) signals 206 to indicate when the next line of image data is to be captured by camera 20. In another form of the invention, camera 20 includes an area sensor array for capturing two-dimensional frames of image data, and trigger generating system 204 generates frame trigger (FT) signals 208 to indicate when the next frame of image data is to be captured by camera 20.

In one embodiment, trigger generating system 204 is coupled to host computer system 26, and receives a trigger position list 205 from computer system 26. Trigger position list 205 is generated by computer system 26, which determines the positions of plate 12 at which image frames should be captured, and stores each such position in the list 205. In one embodiment, trigger position list 205 includes trigger positions for an entire wafer to be inspected. In one form of the invention, trigger position list 205 includes multiple trigger positions of up to one million or more, with each trigger position represented by a 32-bit value. It is to be understood that in some embodiments, the trigger position list 205 may be continuously or discontinuously updated. In one embodiment, the trigger position list 205 is continuously updated by adding new trigger positions, one at a time, in a first-in first-out (FIFO) manner. In another embodiment, the trigger position list 205 is continuously updated by adding groups of multiple new trigger positions, one group at a time. Trigger position list 205 is described in further detail below with reference to FIGS. 3 and 4.

Figure 3:
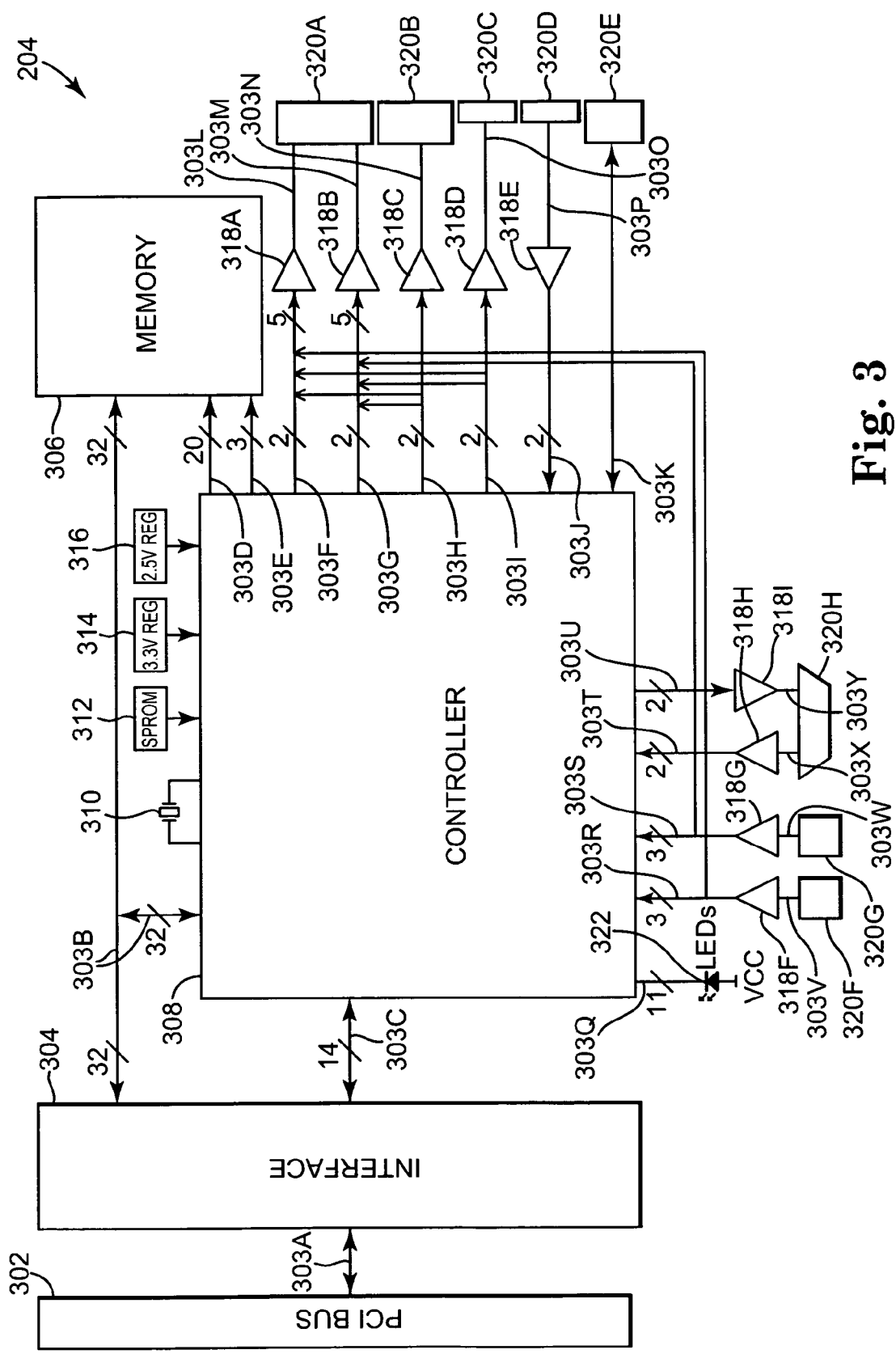
FIG. 3 is a schematic diagram illustrating major components of the trigger generating system shown in FIG. 2 according to one embodiment of the present invention.

FIG. 3 is a schematic diagram illustrating major components of the trigger generating system 204 shown in FIG. 2 according to one embodiment of the present invention. Trigger generating system 204 includes interface 304, memory 306, controller 308, clock signal source 310, static programmable read-only memory (SPROM) 312, voltage regulators 314 and 316, buffers 318A-318I (collectively referred to as buffers 318), connectors 320A-320H (collectively referred to as connectors 320), and light emitting diodes (LED's) 322. The various components of the trigger generating system 304 shown in FIG. 3 are communicatively coupled together via communication links 303A-303Y (collectively referred to as communication links 303).

Also shown in FIG. 3 is a peripheral component interconnect (PCI) bus 302. In one embodiment, PCI bus 302 is included in computer system 26 (FIGS. 1 and 2). In one form of the invention, trigger generating system 204 is implemented in the form of a PCI card that is inserted into a PCI slot within computer system 26, and that communicates with the computer system 26 via the PCI bus 302. In another embodiment, trigger generating system 204 is implemented on a printed circuit board as a stand-alone device separate from computer system 26, and communicates with computer system 26 via a network communication protocol, such as an Ethernet protocol. In one form of the invention, trigger generating system 204 is an operating system independent system.

Interface 304 is coupled to PCI bus 302 via communication link 303A. In one embodiment, interface 304 is an AMCC 5920 32-bit PCI interface from Applied Microsystems Corp. that operates at 33 MHz and that is PCI 2.2 compliant. In one form of the invention, interface 304 is a full read/write interface with memory mapping capabilities, and that does not use interrupts.

Interface 304, memory 306, and controller 308 are coupled to each other via a 32-bit communication link 303B. Interface 304 is also coupled to controller 308 via a 14-bit communication link 303C. Interface 304 receives the trigger position list 205 (FIG. 2) from host computer system 26 via PCI bus 302. Interface 304 transfers the trigger position list 205 to memory 306 via communication link 303B where the trigger position list 205 is stored. In one embodiment, memory 306 is a static random access memory (SRAM) that is 32-bits wide and one megabyte deep.

In one form of the invention, controller 308 is a field programmable gate array (FPGA) that has several modes of operation. In one embodiment, the modes of operation of controller 308 are selected by computer system 26 through interface 304 and communication link 303C. The operation of controller 308 is described in further detail below with reference to FIG. 4.

Figure 4:
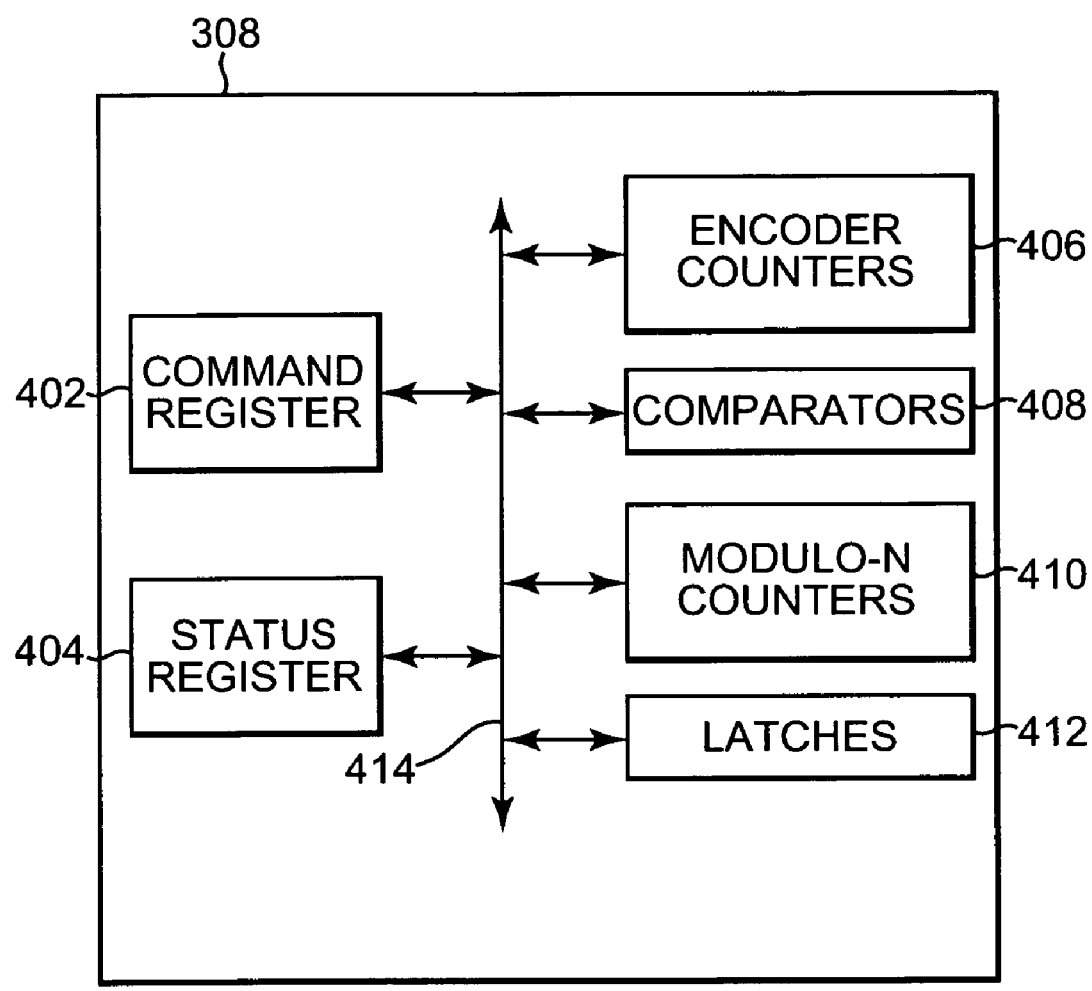
FIG. 4 is a block diagram illustrating major components of the controller shown in FIG. 3 according to one embodiment of the present invention.

FIG. 4 is a block diagram illustrating major components of the controller 308 shown in FIG. 3 according to one embodiment of the present invention. Controller 308 includes command register 402, status register 404, encoder counters 406, comparators 408, modulo-N counters 410, and latches 412, which are communicatively coupled together via communication link 414. In one form of the invention, command register 402 is a 16-bit writeable register, and status register 404 is a 16-bit readable register. In one embodiment, the functionality of controller 308 is programmed by computer system 26 by writing commands to command register 402 via interface 304 and communication link 303C, and by reading status information from status register 404 via interface 304 and communication link 303C.

In one form of the invention, controller 308 includes three encoder channels, one channel for each of the three axes (X, Y, Z) of movement of plate 12. Each encoder channel receives phase A and phase B encoder signals from one of the encoders 202 (FIG. 2), and includes an encoder counter 406, a comparator 408, a modulo-N counter 410, and a latch 412.

Referring again to FIG. 3, Connectors 320D, 320F, and 320G are each configured to be coupled to one of the encoders 202 (FIG. 2). In one embodiment, connectors 320F and 320G are RJ45 connectors that provide encoder signals to buffers 318F and 318G via communication links 303V and 303W, respectively. Buffers 318F and 318G output the encoder signals to controller 308 via 3-bit communication links 303R and 303S, respectively. In one embodiment, connector 320D is an MTA6 connector that provides encoder signals to buffer 318E via communication link 303P. Buffer 318E outputs the encoder signals to controller 308 via 2-bit communication link 303J.

In one form of the invention, controller 308 includes an "encoder" mode of operation and a "modulo-N" mode of operation. The mode of operation is selected by computer system 26 in one embodiment by writing an appropriate command to command register 402. In the encoder mode of operation according to one form of the invention, controller 308 generates frame triggers 208. In the modulo-N mode of operation, controller 308 generates line triggers 206.

In the encoder mode of operation according to one embodiment, the encoder signals received by controller 308 are provided to encoder counters 406. In one embodiment, encoder counters 406 are 27-bit readable and writeable encoder counters that keep an accurate count of the received encoder values up to 20 MHz for a 27-bit counting range. Each encoder counter 406 provides a current count value, which may be read from the encoder counter 406 as a 32-bit value. The current count value of each encoder counter 406 is programmable, and may be set and reset for synchronization purposes.

In one embodiment, motion controller 210 (FIG. 2) also includes a set of encoder counters that receive encoder signals from encoders 202. Thus, the motion controller 210 and the trigger generating system 204 maintain separate counts of the encoder signals. In one form of the invention, the encoder counters of the motion controller 210 and the encoder counters of the trigger generating system 204 are synchronized at a "homing" stage, and then the counters run independently.

In the encoder mode, controller 308 loads a first trigger position value from the trigger position list 205 stored in memory 306 into the comparator 408 for the current encoder channel (i.e., the encoder channel corresponding to the axis to be triggered on). In one embodiment, controller 308 obtains the first trigger position value by sending a READ command to memory 306 on communication link 303E along with a corresponding address on communication link 303D. In response to the READ command, memory 306 outputs the trigger position value to the controller 308 via communication link 303B.

The comparator 408 for the current encoder channel continually compares the current count values generated by the encoder counter 406 for the current encoder channel to the current trigger position value, and determines if a match has occurred. If the comparator 408 determines that a current count value matches (e.g., is equal to) the current trigger position value, controller 308 next determines whether a frame trigger 208 should be generated. In one embodiment, each of the trigger position values in trigger position list 205 is a 27-bit value, with the first 26-bits identifying a position, and the $27^{th}$ bit being a trigger boolean indicating whether a frame trigger 208 should be generated or not. It is to be understood that various bit-length strings may be used in lieu of, or in addition to, the 27-bit value string described herein. For example, in addition to a 27-bit value, 28-32 bit string values, and others may be used. If comparator 408 determines that a current count value matches the current trigger position value, controller 308 generates a frame trigger 208 if the $27^{th}$ bit of the current trigger position value indicates that a trigger is to be generated. If the $27^{th}$ bit of the current trigger position value indicates that a trigger is not to be generated, controller 308 does not generate the frame trigger 208. After a match has occurred, and controller 308 has determined whether or not to generate a frame trigger 208, the next trigger position value in the trigger position list 205 is loaded into the comparator 408 for the current encoder channel, and the above process is repeated.

In one embodiment, controller 308 is configured to latch the current count values generated by encoder counters 406. When controller 308 receives a latch trigger signal, the latch 412 for the current encoder channel latches the current count value generated by the encoder counter 406.

In the modulo-N mode of operation according to one embodiment, the encoder signals received by controller 308 are provided to modulo-N counters 410. In one embodiment, modulo-N counters 410 are 10-bit readable and writeable counters that perform positive and negative counting, and that are used to synchronize a linescan camera to the encoders 202. The letter "N" represents an integer greater than zero. The modulo-N counters 410 act as digital scaling devices that help to ensure the generation of square pixels from the linescan camera. Each modulo-N counter 410 provides a current count value, which may be read from the counter 410 as a 10-bit value. The current count value of each modulo-N counter 410 is programmable. In the modulo-N mode, controller 308 generates line triggers 206 at appropriate times based on the count values generated by modulo-N counters 410.

In one embodiment, controller 308 is configured to output line trigger signals 206 to buffer 318C via 2-bit communication link 303H. The line trigger signals are output from buffer 318C to connector 320B via communication link 303N. In one embodiment, connector 320B is an IDC14 connector.

In one embodiment, controller 308 is configured to output frame trigger signals 208 to buffer 318D via 2-bit communication link 303I. The frame trigger signals are output from buffer 318D to connector 320C via communication link 303O. In one embodiment, connector 320C is an MTA8 connector.

In one form of the invention, controller 308 is configured to output diagnostic information to buffers 318A and 318B via communication links 303F and 303G, respectively. Buffer 318A also receives line trigger signals 206 output by controller 308 on communication link 303H, frame trigger signals 208 output by controller 308 on communication link 303I, and encoder signals output by buffer 318F on communication link 303R. Buffer 318B also receives line trigger signals 206 output by controller 308 on communication link 303H, frame trigger signals 208 output by controller 308 on communication link 303I, and encoder signals output by buffer 318G on communication link 303S. Buffers 318A and 318B output received signals to connector 320A. In one embodiment, connector 320A is an IDC16 connector that is configured to be connected to an oscilloscope or other device to monitor the operation of trigger generating system 204.

Controller 308 is coupled to connector 320E via Joint Test Action Group (JTAG) communication link 303K. In one embodiment, connector 320E is an IDC10 connector. Controller 308 is configured to be programmed by an external device via connector 320E and JTAG communication link 303K.

Buffers 318H and 318I are coupled to connector 320H via communication links 303X and 303Y, respectively. In one embodiment, connector 320H is a DB15 connector. In one embodiment, buffer 318H receives latch trigger signals from connector 320H, and outputs the latch trigger signals to controller 308 via 2-bit communication link 303T. As described above, the latch trigger signals cause the latch 412 for the current encoder channel to latch the current count value generated by the encoder counter 406 for the current encoder channel. Two-bit communication link 303U and buffer 318I are provided for spare output signals from controller 308.

In one form of the invention, controller 308 is configured to drive a plurality of LED's 322 via 11-bit communication link 303Q to provide status information.

Clock signal source 310 provides a 40 MHz clock signal for the digital circuitry within controller 308. Static programmable read-only memory (SPROM) 312 stores control and configuration information that is downloaded to controller 308 at start-up. Voltage regulators 314 and 316 provide a 3.3 volt reference voltage and a 2.5 volt reference voltage, respectively, to circuitry within controller 308.

The trigger generating system 204 according to one embodiment of the present invention is used in one environment to provide a fast (sub-microsecond), deterministic, and arbitrarily programmable, source of machine vision image triggers derived from the position of a moving stage. In one embodiment, the trigger generating system 204 uses its own encoder counters 406 and onboard trigger position list 205 to decouple it from servo cycles or motion controller processing overhead that cause triggers to be delayed or missed in existing DSP and software based trigger generating mechanisms. In one embodiment, the trigger generating system 204 is implemented in hardware, including a controller 308 (e.a., a programmable gate array) and memory 306. The trigger generating system 204 according to one form of the invention provides guaranteed programmable position triggering, with sub-microsecond, deterministic latency, independent of servo cycles or motion controller processing overhead. One embodiment of trigger generating system 204 is faster, more reliable, and can handle a longer trigger list than prior art trigger generators.

Accordingly, the invention as described above and understood by one of skill in the art is simplified, provides an effective, safe, inexpensive, and efficient device, system and process which achieves all the enumerated objectives, provides for eliminating difficulties encountered with prior devices, systems and processes, and solves problems and obtains new results in the art.

In the foregoing description, certain terms have been used for brevity, clearness and understanding; but no unnecessary limitations are to be implied therefrom beyond the requirement of the prior art, because such terms are used for descriptive purposes and are intended to be broadly construed.

Moreover, the invention's description and illustration is by way of example, and the invention's scope is not limited to the exact details shown or described.

Having now described the features, discoveries and principles of the invention, the manner in which it is constructed and used, the characteristics of the construction, and the advantageous, new and useful results obtained; the new and useful structures, devices, elements, arrangements, parts and combinations, are set forth in the appended claims.

What is claimed is:

1. A system for generating a camera trigger that causes a camera to capture image data, comprising:
   a memory for storing a plurality of trigger values at a time, each trigger value corresponding to a position of a moving stage at which an image is to be captured, the plurality of trigger values thereby identifying a plurality of different positions at which a plurality of images are to be captured;
   a controller for receiving position information indicative of a current position of the moving stage, generating a current position value based on the position information, comparing the current position value to at least one of the trigger values, and generating a camera trigger if the current position value matches one of the trigger values, wherein the generated camera trigger is configured to cause the camera to capture image data; and
   wherein the memory and the controller are separate and distinct from a motion controller that controls motion of the moving stage, and from a computer system that processes images captured by the camera, and wherein the stored plurality of trigger values is updated by adding multiple trigger values to the stored plurality of trigger values during automated inspection of a moving object positioned on the moving stage.

2. The system of claim 1, wherein the controller is a field programmable gate array (FPGA).

3. The system of claim 1, wherein the controller includes an encoder counter for receiving encoder signals indicative of the current position of the moving stage, and wherein the encoder counter is configured to generate the current position value based on the received encoder signals.

4. The system of claim 1, wherein the controller includes a comparator for comparing the current position value to at least one of the trigger values.

5. The system of claim 1, wherein the camera trigger is a frame trigger for causing the camera to capture a two-dimensional frame of image data.

6. The system of claim 1, wherein the controller includes a modulo-N counter, and wherein the controller is configured to generate line triggers for causing the camera to capture lines of image data based on an output of the modulo-N counter, where N is an integer greater than zero.

7. The system of claim 1, wherein the controller includes a command register for receiving commands from a host device, and a status register for providing status information to the host device.

8. The system of claim 1, wherein the memory is a static random access memory (SRAM).

9. The system of claim 8, wherein the SRAM is at least about 32-bits wide and at least about one megabyte deep.

10. The system of claim 1, wherein the memory and the controller are implemented on a peripheral component interconnect (PCI) card that is configured to be inserted into a host device.

11. The system of claim 1, wherein the memory and the controller are implemented as a standalone device that is separate from a host device, and wherein the standalone device is configured to communicate with the host device via a network communication protocol.

12. The system of claim 1, wherein the plurality of trigger values include at least 100,000 different trigger values.

13. The system of claim 1, wherein the plurality of trigger values include at least one million different trigger values.

14. The system of claim 1, wherein the plurality of trigger values are continuously updated.

15. The system of claim 14, wherein the plurality of trigger values are continuously updated by adding new trigger values in a first-in first-out (FIFO) manner.

16. The system of claim 14, wherein the plurality of trigger values are updated in groups of multiple trigger values at a time.

17. The system of claim 1, wherein the system is operating system independent.

18. A method of generating a camera trigger that causes a camera to capture image data, comprising:
  storing a plurality of trigger values at a time in a memory, each trigger value corresponding to a position of a moving stage at which an image is to be captured, the plurality of trigger values thereby identifying a plurality of different positions at which a plurality of images are to be captured;
  receiving position information indicative of a current position of the moving stage;
  generating a current position value based on the position information;
  comparing the current position value to at least one of the trigger values;
  generating a camera trigger if the current position value matches one of the trigger values, wherein the generated camera trigger is configured to cause the camera to capture image data; and
  updating the plurality of stored trigger values by adding multiple trigger values at a time to the memory during automated inspection of a moving object positioned on the moving stage.

19. The method of claim 18, wherein the steps of receiving position information, generating a current position value, comparing the current position value, and generating a camera trigger, are performed by a field programmable gate array (FPGA).

20. The method of claim 18, wherein the generated camera trigger is a frame trigger for causing the camera to capture a two-dimensional frame of image data.

21. The method of claim 18, and further comprising:
  generating line triggers for causing the camera to capture lines of image data based on an output of a modulo-N counter, where N is an integer greater than zero.

* * * * *